United States Patent [19]

Unger

[11] Patent Number: 5,320,826
[45] Date of Patent: Jun. 14, 1994

[54] PHOSPHORYLATED MATERIALS AS CONTRAST AGENTS FOR USE IN MAGNETIC RESONANCE IMAGING OF THE GASTROINTESTINAL REGION

[76] Inventor: Evan C. Unger, 13365 E. Camino La Cebadilla, Tucson, Ariz. 85749

[21] Appl. No.: 867,166

[22] Filed: Apr. 10, 1992

Related U.S. Application Data

[62] Division of Ser. No. 649,437, Feb. 1, 1991, Pat. No. 5,143,716.

[51] Int. Cl.$^5$ .................. A61B 5/055; C07F 9/02; A61K 31/66
[52] U.S. Cl. ........................... 424/9; 436/173; 556/15; 556/16; 556/18; 514/114; 514/836; 568/10; 128/653.4
[58] Field of Search ............ 424/9; 436/173; 568/10; 514/836, 114; 128/653.4, 654; 556/15, 16, 18

[56] References Cited

U.S. PATENT DOCUMENTS

| | | | |
|---|---|---|---|
| 4,532,217 | 7/1985 | Springer, Jr. et al. | 436/79 |
| 4,615,879 | 10/1986 | Runge et al. | 424/9 |
| 4,647,447 | 3/1987 | Gries et al. | 424/9 |
| 4,719,098 | 1/1988 | Weinmann et al. | 424/9 |
| 4,749,560 | 7/1988 | Elgavish | 424/9 |
| 4,867,963 | 9/1989 | Maurer et al. | 424/9 |
| 4,880,007 | 11/1989 | Sadler et al. | 128/653 |
| 4,909,257 | 3/1990 | Engelstad et al. | 128/654 |
| 4,915,933 | 4/1990 | Matwiyoff | 424/9 |
| 4,983,376 | 1/1991 | Sherry | 424/9 |
| 4,986,980 | 1/1991 | Jacobsen | 424/9 |

FOREIGN PATENT DOCUMENTS

| | | |
|---|---|---|
| 0186947A1 | 7/1986 | European Pat. Off. . |
| WO91/07911 | 6/1991 | PCT Int'l Appl. . |

OTHER PUBLICATIONS

Hack's Chemical Dictionary; 4th Ed. p. 25 (1969).
Webster's International Dictionary 2nd Ed (1950) p. 66.
Morrison & Boyd; Organic Chemistry 3rd Ed. (1973) p. 318.
Winchell et al., Chem. Abs. 116(7): 54742a (1991).
Bales et al., Nutritional Bioavailability of Manganese, Ch. 11, pp. 112–122 (American Chemical Society, Washington, D.C. 1987).
Bothwell et al., Journal of Internal Medicine, vol. 226, pp. 357–365 (1989).
Bothwell et al., Iron Metabolism in Man, Ch. 12, (Blackwell Scientific Publications, Oxford, England 1979).
Breitenbach et al., in Phytic Acid: Chemistry and Applications, pp. 127–130, Graf, ed., (Pilatus Press, Minneapolis, Minn. 1986).
Davies et al., British Journal of Nutrition, vol. 34, pp. 243–258 (1975).
Gruden, Nutritional Bioavailability of Manganese, Ch. 7, pp. 67–79, Kies, ed. (American Chemical Society, Washington D.C. 1987).
Hallberg et al., American Journal of Clinical Nutrition, vol. 49, pp. 140–144 (1989).
Hallberg et al., American Journal of Clinical Nutrition, vol. 45, pp. 988–996 (1987).
Hurley, Clinical, Biochemical and Nutritional Aspects of Trace Elements, Ch. 20, pp. 369–378, Prasad, ed. (Alan R. Liss, Inc. 1982).
D. M. Kean and M. A. Smith, Magnetic Resonance Imaging: Principles and Applications, (Williams and Wilkins, Baltimore 1986).
Kennedy et al., J. Appl. Chem., vol. 8, pp. 459–464 (1958).

(List continued on next page.)

Primary Examiner—Gary E. Hollinden
Attorney, Agent, or Firm—Woodcock Washburn Kurtz Mackiewicz & Norris

[57] ABSTRACT

Methods of providing an image of the gastrointestinal region of a patient and diagnosing the presence of any tumorous tissue in that region using contrast media comprising a combination of at least one polyphosphorylated aliphatic or polyphosphorylated alicyclic compound and at least one paramagnetic ion, wherein the aliphatic and alicyclic compounds comprise at least five carbon atoms, is described. Also described are diagnostic kits for gastrointestinal imaging which include the subject contrast media.

12 Claims, 10 Drawing Sheets

OTHER PUBLICATIONS

Kies, *Nutritional Bioavailability of Manganese*, Ch. 1, pp. 1–8, Kies, ed. (American Chemical Society, Washington, D. C. 1987).

Kies et al., *Nutritional Bioavailability of Manganese*, Ch. 13, pp. 136–145, Kies, ed. (American Chemical Society, Washington, D.C. 1987).

Leonard et al., *J. App. Polymer Sci.*, vol. V, pp. 157–162 (1961).

Leonard et al., *J. of Polymer Sci.*, vol. 55, pp. 799–810 (1961).

Maddaiah et al., *Proc. Soc. Exp. Biol. Med.*, vol. 115, pp. 391–393 (1964).

Marvel et al., *J. of Polymer Sci.*, vol. VIII, pp. 495–502 (1952).

Morris, E. R., *Phytic Acid: Chemistry and Application*, Ch. 4, pp. 57–76, Graf, ed. (Pilatus Press, Minneapolis, Minn. 1986).

Reddy et al., *Phytates in Cereals and Legumes*, Ch. 7, pp. 57–70 (CRC Press, Inc., Boca Raton, Fla. 1989).

Reddy et al., *Phytates in Cereals and Legumes*, Ch. 9, pp. 81–110 (CRC Press Inc., Boca Raton, Fla. 1989).

Sander et al., *J. Macromol. Sci., Rev. Macromol. Chem.*, vol. 2, pp. 57–72 (1968).

Schroeder et al., *J. of Polymer Sci.*, vol. XLVII, pp. 417–433 (1950).

Thomson et al., *J. Lab. and Clin. Med.*, vol. 78, pp. 642–655 (1971).

Vohra et al., *Proc. Soc. Exp. Biol. Med.*, vol. 120, pp. 447–449 (1965).

Conti, F. et al., *Chemical Abstracts*, vol. 108, No. 108916r (1988).

Sadler, P. J. et al., *Chemical Abstracts*, vol. 111, No. 74025u (1989).

Pilgrimm, H., *Chemical Abstracts*, vol. 112, No. 51778y (1990).

PHOSPHORYLATED MATERIALS AS CONTRAST AGENTS FOR USE IN MAGNETIC RESONANCE IMAGING OF THE GASTROINTESTINAL REGION

This is a division of application Ser. No. 07/649,437, filed Feb. 1, 1991 now U.S. Pat. No. 5,143,716.

BACKGROUND OF THE INVENTION

Magnetic Resonance Imaging (MRI) is a relatively new diagnostic imaging technique which employs a magnetic field, field gradients and radiofrequency energy to excite protons and thereby make an image of the mobile protons in water and fat. MRI has found many applications in imaging the central nervous system, but abdominal applications have lagged seriously behind. One reason that abdominal MRI has not been utilized more extensively has been the absence of a suitable MRI contrast agent for the gastrointestinal tract. Computed tomography (CT) is used more commonly for abdominal imaging in part because suitable contrast agents, chiefly barium and iodine compounds, are available for use in such imaging.

MRI contrast agents primarily act by affecting T1 or T2 relaxation of water protons. Contrast agents generally shorten T1 and/or T2. When contrast agents shorten T1, this increases signal intensity on T1 weighted images. When contrast agents shorten T2, this decreases signal intensity particularly on T2 weighted pulse sequences. To date several prototype gastrointestinal MRI contrast agents have been developed to assist abdominal MRI, but none of these have been altogether satisfactory.

For example, iron oxides which are strong T2 relaxation agents have been used as negative gastrointestinal MRI contrast agents to decrease signal intensity in the gastrointestinal tract. These agents, which predominantly affect T2, have the disadvantages of magnetic susceptibility artifacts which occurs as a result of the drastic effects on local magnetic homogeneity (magnetic susceptibility) caused by these agents. Magnetic susceptibility artifacts make it difficult to assess the bowel wall, bowel mesentery and adjacent structures.

The paramagnetic MRI contrast agent gadolinium-DTPA has also been tested as a positive gastrointestinal MRI contrast agent to increase signal intensity on T1 weighted images, but this agent has the drawback that decomplexation and release of free gadolinium ion may occur in the gastrointestinal tract which can be quite toxic. Furthermore, gadolinium-DTPA is relatively expensive.

Ferric iron has also been experimented with as an oral gastrointestinal MRI contrast agent. Ferric iron has been administered in the form of ferric ammonium citrate wherein the paramagnetic $Fe^{+3}$ iron relaxes the water in bowel to make the bowel bright on T1 weighted images. Ferric ammonium citrate is quite inexpensive but the resultant gastrointestinal MRI contrast agent has been suboptimally useful. To obtain reasonable contrast enhancement, a relatively high dose of ferric iron is required, and some of this iron is absorbed as it passes down the gastrointestinal tract. Absorption of the iron creates two problems. First, absorption of the iron may cause problems with iron toxicity and iron overload. Second, as the iron is absorbed from the gastrointestinal tract, the concentration of the contrast agent decreases and the degree of contrast enhancement is much less in the distal bowel.

The ideal contrast agent for the gastrointestinal tract would affect both T1 and T2, causing the tract lumen to appear bright on T1 weighted images and dark on T2 weighted images. Tumors and other pathologic tissues generally have a long T1 and a long T2, which is to say that these pathologic tissues appear dark on T1 weighted images and bright on T2 weighted images. If the lumen could be filled with contrast material which appeared bright on T1 weighted images and dark on T2 weighted images, it would then be easy to differentiate a normal gastrointestinal tract from any adjacent abnormal tissues. The ideal contrast agent would also serve to minimize any toxicity problems, and be relatively inexpensive.

The need is great for new gastrointestinal MRI contrast agents, having some or all of the aforementioned qualities. The present invention is directed to achieving this important end.

SUMMARY OF THE INVENTION

The present invention is directed to magnetic resonance imaging, and more particularly to the use of a contrast medium comprising a combination of at least one polyphosphorylated aliphatic or alicyclic compound of five or more carbon atoms and at least one paramagnetic ion to image the gastrointestinal region of a patient.

Specifically, the present invention pertains to methods of providing an image of the gastrointestinal region of a patient comprising (i) administering to the patient the aforementioned contrast medium, and (ii) scanning the patient using magnetic resonance imaging to obtain visible images of that region.

The present invention is further directed to methods for diagnosing the presence of diseased tissue in the gastrointestinal region of a patient comprising (i) administering to the patient the aforementioned contrast medium, and (ii) scanning the patient using magnetic resonance imaging to obtain visible images of any diseased tissue in the patient.

The present invention also provides diagnostic kits for gastrointestinal imaging which include the subject contrast medium.

The polyphosphorylated compounds, when employed in combination with paramagnetic ions, provide highly effective and relatively inexpensive contrast enhancement agents for gastrointestinal magnetic resonance imaging. Unlike many of the gastrointestinal agents of the prior art, where contrast enhancement has been either positive or negative, the present invention provides a contrast agent that may impart both positive and negative contrast. The polyphosphorylated compounds used in the present invention serve to effectively bind the paramagnetic ion, thereby minimizing the potential for absorption of potentially toxic paramagnetic ion throughout the gastrointestinal region. This means that not only can a lower dose of paramagnetic ion be used for contrast enhanced magnetic resonance imaging than would be possible without polyphosphorylated compounds, but also that a relatively uniform concentration of the ion can be achieved throughout the gastrointestinal tract. Moreover, the polyphosphorylated compounds utilized in the present invention have been found to enhance the relaxivity of the paramagnetic ions. In the case of the combination of the polyphosphorylated compound inositol hexaphosphate with the paramagnetic agent ferric iron, for example, relaxivity in the gastrointestinal region was found to increase by a factor of almost three-fold in comparison with the use of ferric iron alone. Simultaneously, the absorption of ferric iron in the gastrointestinal tract was found to decrease by over 80%. Heretofore, the use of such agents for gastrointestinal imaging and the safe and highly effective contrast enhancement achieved thereby, was neither disclosed nor suggested.

These and other aspects of the invention will become more apparent from the following detailed description when taken in conjunction with the following figures.

DETAILED DESCRIPTION OF THE INVENTION

Any of the wide variety of biocompatible polyphosphorylated aliphatic or alicyclic compounds of at least five carbon atoms that are known in the art may be employed in the methods and kits of the present invention. The term biocompatible, used throughout the specification, is employed in its conventional sense, that is, to denote compounds that do not substantially interact with the tissues, fluids and other components of the body in an adverse fashion in the particular application of interest. The term polyphosphorylated, used in connection with the compounds of the present invention, denotes compounds containing two or more phosphate (e.g., $PO_4^{-3}$, $PO_3H^{-1}$ or $PO_2H^{-2}$) substituents. The terms aliphatic and alicylic, used herein, are employed in the conventional sense, that is, aliphatic denotes herein organic compounds having an open chain structure, and alicyclic denotes herein organic compounds having a saturated ring structure.

Preferably, the polyphosphorylated compounds of the invention contain at least three phosphate groups, more preferably at least four phosphate groups, even more preferably at least five phosphate groups, and most preferably at least six phosphate groups. In the case of poly- phosphorylated alicyclic compounds, it is preferable that the phosphate groups be located both above and below the plane of the ring, that is, one pair of phosphate groups are located trans to one another. Also, in the case of aliphatic compounds, the compound is preferably at least about ten carbon atoms in length, more preferably at least about fifteen carbon atoms in length, even more preferably at least about twenty carbon atoms in length, and most preferably at least about thirty carbon atoms in length. Preferably, the molecular weight of the phosphorylated aliphatic compound would be in the range of about 20,000 to about 100,000, most preferably between about 50,000 and about 100,000. In the case of alicyclic compounds, the cyclic compound preferably contains at least six carbon atoms in its ring structure, and there may, if desired, be more than one carbon ring structure in tandem, that is dimers (e.g., disaccharides), trimers, oligomers, and polymers (e.g., polysaccharides). As will be readily apparent to those skilled in the art, once armed with the present disclosure, there are a number of polyphosphorylated compounds that can be effectively employed in the present invention, and any of such compounds, as well as any combinations thereof are intended to be within the scope of the present invention.

Suitable biocompatible polyphosphorylated aliphatic compounds of at least five carbon atoms include biocompatible aliphatic compounds which may be polyphosphorylated, such as biocompatible aliphatic compounds containing hydroxyl, keto, amino, or unsaturated groups. Such biocompatible aliphatic compounds include, but are not limited to, polyphosphorylated polyvinyl alcohol, polyphosphorylated polyethylene glycol, polyphosphorylated polypropylene glycol, polyphosphorylated polystyrene, polyphosphorylated polyacrylic acid, polyphosphorylated polymethacrylic acid, polyphosphorylated copolymers of acrylic and methacrylic acid, and various polyphosphorylated polyolefins.

Suitable biocompatible polyphosphorylated alicyclic compounds of at least five carbon atoms include, but are not limited to: polyphosphorylated sugar alcohols such as polyphosphorylated inositol, polyphosphorylated mannitol, polyphosphorylated sorbitol, polyphosphorylated pentaerythritol, polyphosphorylated galacitol, polyphosphorylated adonitol, polyphosphorylated arabitol, and polyphosphorylated xylitol; polyphosphorylated monosaccharides such as polyphosphorylated glucose, polyphosphorylated fructose, polyphosphorylated mannose, polyphosphorylated idose, polyphosphorylated galactose, polyphosphorylated allose, polyphosphorylated altrose, and polyphosphorylated arabinose; polyphosphorylated disaccharides such as polyphosphorylated sucrose, polyphosphorylated maltose, polyphosphorylated cellobiose, and polyphosphorylated lactose; and polyphosphorylated polysaccharides such as polyphosphorylated cellulose, polyphosphorylated agarose, polyphosphorylated lignan, and polyphosphorylated chitin.

For reasons of diagnostic efficacy and biocompatibility, polyphosphorylated inositol and/or polyphosphorylated cellulose compounds are most preferred.

Such polyphosphorylated aliphatic and alicyclic compounds can be easily prepared from readily available starting materials, using conventional synthesis techniques, as will be apparent to those skilled in the art. Conventional phosphorylating agents include such compounds as phosphorous chloride (mono-, di-, or tri-), phosphorous bromide (mono-, di-, or tri-), phosphorous oxychloride (mono-, di-, or tri-), phosphorous oxybromide (mono-, di-, or tri-), phosphorous pentaoxide, phosphoric acid, phosphorous acid, and the anhydrides thereof, pyrophosphoric acid, aziridine phosphine oxide, choloroalkylphosphonic acid or its derivatives, and phosphorous acid ester.

In accordance with one preparatory protocol, starting with an aliphatic or alicyclic compound containing one or more hydroxyl groups, for example, phosphorylation can be easily carried out by suspending the starting material in, for example, chloroform, then adding a phosphoric ester monochloride compound to the suspension, preferably dropwise. Suitable phosphoric ester monochloride compounds include $ClP(O)(OR)_2$, wherein R is selected from, inter alia, $C(O)CH_3$, $C(O)H$, $CH_3$, $C_2H_5$, $C_3H_7$, $C_4H_9$, and $CH_2C_6H_5$. The resulting phosphorylated compound can then be treated with water to hydrolyze to the corresponding phosphonic acid derivatives. Such hydrolyzed derivatives are included within the scope of the phrase phosphorylated compounds herein.

In another method for preparing the phosphorylated aliphatic and alicylic compounds of the invention, the urea catalyzed phosphoric acid (or phosphorous acid) phosphorylation procedures may be conveniently utilized. In this procedure, aliphatic or alicyclic compounds are soaked with mixtures of urea and phosphoric acid (or phosphorous acid), then heated to 120° C., or higher.

In a further method, phosphorylation of compounds such as polyvinyl alcohol can be carried out by dissolving the polyvinyl alcohol in an organic solvent such as pyridine, dimethylformamide, or dimethylsulfoxide with triethylamine, and then adding dialkyloxyphosphoric monochloride (($RO)_2POCl$) to the solution. After phosphorylation the solutions are hydrolyzed by adding water and acidifying with hydrochloric acid. Unbound phosphorous is then removed by passing the solution through a column filled anion exchanger.

Other methods of phosphorylating various compounds to produce phosphorylated compounds within the scope of the present invention are disclosed, for example, in Sander et al., *J. Macromol. Sci., Rev. Macromol. Chem.*, Vol. 2, pp. 57–72 (1968), Leonard et al., *J. of Polymer Sci.*, Vol. V, pp. 157–162 (1961), Leonard et al., *J. of Polymer Sci.*, Vol. 55, pp. 799–810 (1961), Schroeder et al., *J. of Polymer Sci.*, Vol. XLVII, pp. 417–433 (1960), Kennedy et al., *J. Appl. Chem.*, Vol. 8, pp. 459–464 (1958), Marvel et al., *J. of Polymer Sci.*, Vol. VIII, pp. 495–502 (1952), the disclosures of each of which are hereby incorporated herein by reference, in their entirety.

As a general matter, it is believed that the higher the degree of phosphorylation in the aliphatic and alicyclic compounds, the more diagnostically effective and less toxic is the contrast medium when employed as a gastrointestinal contrast agent. For example, although all polyphosphorylated inositol compounds can be employed in the imaging methods of the invention, inositol hexaphosphate is preferred over inositol pentaphosphate, which in turn is preferred over inositol tetraphosphate, which in turn is preferred over inositol triphosphate. It is also believed that, for reasons of diagnostic efficacy, a larger carbon chain is preferred over a smaller one. Thus, for example, a six carbon containing alicyclic compound such as inositol polyphosphate is preferred over a five carbon containing alicyclic compound such as arabinose polyphosphate, and a thirty carbon aliphatic compound such as a thirty carbon polyvinyl alcohol is preferred over a twenty carbon aliphatic compound such as a twenty carbon polyvinyl alcohol.

As noted above, the polyphosphorylated aliphatic and alicyclic compounds are employed in combination with paramagnetic ions. Suitable paramagnetic ions include, but are not limited to, compounds comprising transition, lanthanide and actinide elements, and any of the suitable paramagnetic ions, and any combinations thereof, are intended to be within the scope of the present invention. Preferable of such elements are Gd(III), Mn(II), Cu(II), Cr(III), Fe(II), Fe(III), Co(II), Er(II), Ni(II), Eu(III), Yb(III) and Dy(III). More preferably, the elements are Fe(III), Gd(III), Mn(II), Cu(II), Cr(III), Yb(III) and Dy(III), especially Fe(III) and Mn(II). The paramagnetic ions may be added, if desired, as a salt, such as, for example, in the case of ferric iron (Fe(III)), as ferric citrate, ferric chloride, ferric acetate, ferric glycerophosphate, ferric sulfate, ferric phosphate, and ferric ammonium phosphate. The preferable paramagnetic ions are Fe(III), added in the form of ferric citrate, and Mn(II), added in the form of manganese chloride, manganese acetate, manganese sulfate or manganese phosphate.

As noted above, combinations of paramagnetic ions are within the scope of the present invention. Choice of appropriate combinations of paramagnetic ions can increase the ultimate relaxivity and contrast enhancement of the contrast media of the present invention. By way of example, an extremely good combination of paramagnetic ions for the contrast media of the present invention are manganese and iron. This combination takes into account the fact that manganese is a better contrast agent than iron, that both are absorbed from the gastrointestinal tract through similar receptors, and that iron is preferentially absorbed over manganese, a competitive absorption type of situation. The inclusion of the iron would thus serve to minimize any absorption of the more active manganese, resulting in a better contrast medium. This phenomenon is shown in Examples 6 and 7, below.

As one skilled in the art would recognize, wide variations in the amounts of the polyphosphorylated compound and paramagnetic ion can be employed in the methods and kits of the invention, with the precise amounts varying depending upon such factors as the mode of administration (e.g., oral, rectal), and the specific portion of the gastrointestinal tract for which an image is sought (e.g., the esophagus, stomach, rectum, etc). Preferably, however, the paramagnetic ions are present in a concentration between about 1 to about 4 millimolar. The polyphosphorylated compounds are preferably present in a molar concentration of between about 0.1 and about 3 times the molar concentration of the paramagnetic ions. Most preferably, the molar concentration of the polyphosphorylated alicyclic compounds is about 1.0 times the molar concentration of the paramagnetic ions. Most preferably, the molar concentration of the phosphorylated aliphatic compounds is between about 0.1 and about 0.5 times the molar concentration of the paramagnetic ions. The volume of contrast agent administered to the gastrointestinal tract is preferably between about 500 to about 1000 cc, and is supplied in the form of an aqueous solution.

The polyphosphorylated compounds and paramagnetic ion compositions may be employed alone, if desired, as a contrast medium for gastrointestinal magnetic resonance imaging. Alternatively, if desired, they may be employed in conjunction with other biocompatible synthetic or natural polymers. By the phrase in conjunction with it is meant that the polymers may be simply added to the polyphosphorylated compound and paramagnetic ion mixture, or alternatively may be bound to the polyphosphorylated compound by a covalent linkage, the binding being accomplished using conventional methodology, such as, for example, by the procedures described in Breitenbach et al., in *Phytic Acid: Chemistry and Applications*, pp. 127–130, Graf, ed., (Pilatus Press, Minneapolis, Minn. 1986), the disclosures of which are incorporated herein by reference in their entirety. Exemplary suitable synthetic polymers include polyethylenes (such as, for example, polyethylene glycol), polyoxyethylenes (such as, for example, polyoxyethylene glycol), polypropylenes (such as, for example, polypropylene glycol), pluronic acids and alcohols, polyvinyls (such as, for example, polyvinyl alcohol), and polyvinylpyrrolidone. Exemplary suitable natural polymers include polysaccharides. Such polysaccharides include, for example, arabinans, fructans, fucans, galactans, galacturorans, glucans, mannans, xylans (such as, for example, inulin), levan, fucoidan, carrageenan, galactocarolose, pectic acid, amylose, pullulan, glycogen, amylopectin, cellulose, carboxylmethylcellulose, hydroxypropyl methylcellulose, dextran, pustulan, chitin, algin, agarose, keratan, chondroitin, dermatan, hyaluronic acid and alginic acid, and various other homopolymers or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid. Algin has been found to be a particularly useful polymer to use in conjunction with the contrast media of the invention because this compound, which binds about 300 times its weight in water and has a slippery texture, hastens gastrointestinal transit and promotes gastric emptying. Its use in conjunction with the contrast media of the invention is illustrated in Example 7, below. As those skilled in the art will recognize armed with the present disclosure, such polymers may be added in varying amounts, as desired.

The polyphosphorylated compounds and paramagnetic ion compositions of the invention may also be employed, if desired, with other agents which effect T2 relaxation such as bismuth, barium, kaolin, atapulgite, ferric oxide (either uncoated or coated with, for example, dextran, algin, cellulose, etc., for improving the suspension of the ferric oxide particles), or stabilized gas (stabilized with, for example, microspheres of polyvinylidene acrylonitrile copolymers or acrylonitrile polymers of about 20 to about 100 microns in size).

If desired, in addition, the contrast medium of the present invention may be utilized with biocompatible anti-oxidant compounds. Suitable anti-oxidants include vitamin C (ascorbic acid), vitamin E (tocopherol), and retinoic acid. Other suitable anti-oxidants will be readily apparent to those skilled in the art. The anti-oxidants may be employed in certain applications to keep paramagnetic ions, such as manganese, in their more paramagnetically effective reduced state, that is, for example, in the Mn(II) state, rather than the Mn(III) state.

The contrast medium utilized in the gastrointestinal applications of the present invention may also be employed with conventional biocompatible anti-gas agents. As used herein the term anti-gas agent is a compound that serves to minimize or decrease gas formation, dispersion and/or adsorption. A number of such agents are available, including antacids, antiflatulents, antifoaming agents, and surfactants. Such antacids and antiflatulents include, for example, activated charcoal, aluminum carbonate, aluminum hydroxide, aluminum phosphate, calcium carbonate, dihydroxyaluminum sodium carbonate, magaldrate magnesium oxide, magnesium trisilicate, simethicone, sodium carbonate, loperamide hydrochloride, diphenoxylate, hydrochloride with atropine sulfate, Kaopectate TM (kaolin) and bismuth salts. Suitable antifoaming agents useful as anti-gas agents include simethicone, protected simethicone, siloxyalkylene polymers, siloxane glycol polymers, polyoxypropylene-polyoxyethylene copolymers, polyoxyalkylene amines and imines, branched polyamines, mixed oxyalkylated alcohols, finely divided silica either alone or mixed with dimethyl polysiloxane, sucroglycamides (celynols), polyoxylalkylated natural oils, halogenated silicon-containing cyclic acetals, lauryl sulfates, 2-lactylic acid esters of unicarboxylic acids, triglyceride oils. Particles of polyvinyl chloride or silica may also function as anti-foaming agents in the subject invention. Suitable surfactants include perfluorocarbon surfactants, such as, for example, DuPont Zonyl ™ perfluoroalkyl surfactants known as Zonyl ™ RP or Zonyl ™ NF, available from DuPont, Chemicals and Pigments Division, Jackson Laboratory, Deepwater, N.J. 08023. Of course, as those skilled in the art will recognize, any anti-gas agents employed must be suitable for use within the particular biological system of the patient in which it is to be used. The concentration of such anti-gas agents may vary widely, as desired, as will be readily apparent to those skilled in the art. Typically, however, such agents are employed in concentrations of between about 20 and about 2000 ppm, most preferably in concentrations between about 50 and about 1000 ppm.

The present invention is useful in imaging the gastrointestinal region of a patient and in diagnosing the presence of diseased tissue in that region. The imaging process of the present invention may be carried out by (a) administering to a patient a contrast medium comprising (i) at least one polyphosphorylated compound comprising at least five carbon atoms, and (ii) at least one paramagnetic ion, and (b) then scanning the patient using magnetic resonance imaging to obtain visible images of the gastrointestinal region of a patient and/or of any diseased tissue in that region. The phrase gastrointestinal region or gastrointestinal tract, as used herein, includes the region of a patient defined by the esophagus, stomach, small and large intestines, and rectum. The patient can be any type of mammal, but most preferably is a human.

As one skilled in the art would recognize, administration may be carried out in various fashions, such as orally, rectally, intravascularly, using a variety of dosage forms. Since the region to be scanned is the gastrointestinal region, administration of the contrast medium of the invention is preferably carried out orally or rectally. The useful dosage to be administered and the particular mode of administration will vary depending upon the age, weight and the particular mammal to be scanned, the particular portion of the gastrointestinal region to be scanned, and the particular contrast medium to be employed. Typically, dosage is initiated at lower levels and increased until the desired contrast enhancement is achieved. If desired, a multiple dosing method of delivering the contrast agents of the invention may be employed to provide uniformity of enhancement throughout the gastrointestinal tract, such as is illustrated in Examples 6 and 7, below.

Kits useful for magnetic resonance imaging of the gastrointestinal region in accordance with the present invention comprise at least one phosphorylated compound comprising at least five carbon atoms and at least one paramagnetic ion, in addition to conventional proton magnetic resonance imaging kit components. Such conventional proton magnetic resonance imaging kit components include those described above, as well as other components which will be readily apparent to those skilled in the art, once armed with the present disclosure, such as those described in Weinmann et al., U.S. Pat. No. 4,719,098, the disclosures of which are hereby incorporated by reference in their entirety. Exemplary components which may be employed in the kit in addition to the phosphorylated compounds comprising at least five carbon atoms and the paramagnetic ions, include polymers, anti-oxidants, anti-gas agents, various T2 relaxation agents, osmolality raising agents, viscosity and bulking agents, buffering agents, and gastrointestinal transit agents to decrease gastrointestinal transit time and increase rate of gastrointestinal emptying.

Such kit components as polymers, anti-oxidants, anti-gas agents, and T2 relaxation agents have been described in detail above.

Suitable osmolality raising agents include polyols and sugars, for example, mannitol, sorbitol, arabitol, xylitol, glucose, sucrose, fructose, and saccharine, with mannitol and sorbitol being most preferred. The concentration of such osmolality raising agents may vary, as desired, however, generally a range of about 5 to about 70 g/l, preferably about 30 to about 50 g/l of the contrast medium. Such compounds may also serve as sweeteners for the ultimate formulation, if desired.

Suitable viscosity and bulking agents include the polymers described in detail above, as well as other agents which are well known in the art to provide viscosity and bulking. Particularly useful are alginates, xanthan gum, guar, pectin, tragacanth, bassorin, karaya, gum arabic, casein, gelatin, sodium carboxymethylcellulose, methylcellulose, methylhydroxycellulose, bentonite, collodial silicic acid, and various anti-diarrhetic preparations. Such compounds may be employed in varying amounts, as those skilled in the art would recognize, but preferably are employed in amounts of about 2 to about 40 g/l, preferably about 10 to about 30 g/l of the contrast medium.

Buffering agents, that is buffers, buffer mixtures and bases, may be utilized to stabilize the phosphorylated compound and paramagnetic ion complex with respect to the acidic stomach content. Such buffering agents include tris(hydroxymethyl)aminomethane (2-amino-2-hydroxymethyl-1,3-propanediol, trometamol), sodium dihydrogen phosphate/disodium hydrogen phosphate, citric acid/disodium phosphate, etc., with trometamol being preferred. Other suitable buffering agents include all physiologically compatible organic and inorganic bases, e.g., sodium carbonate, calcium carbonate, amino sugars (e.g., glucosamine), amino alcohols (e.g., methylglucamine), amino acids (e.g., arginine, lysine), and the like. The desired pH range is about 3 to about 9 pH units, preferably about 4 to about 9 pH units in the gastrointestinal region to be imaged. In view of the strong binding capabilities, relatively speaking, of the phosphorylated compounds, such buffering agents may be unnecessary. If employed, the buffering agents may be used in varying amounts, as will be readily apparent to those skilled in the art, generally in concentrations between about 5 and about 40 mmol/l.

Gastrointestinal transit agents to decrease gastrointestinal transit time and increase rate of gastrointestinal emptying include algin, as well as many of the compounds listed above as viscosity and bulking agents, with algin being most preferred. The amount of such agents will, of course, vary as those skilled in the art will recognize, but generally will be employed in an amount of between about 5 and about 40 mmol/l.

The magnetic resonance imaging techniques which are employed are conventional and are described, for example, in D. M. Kean and M. A. Smith, *Magnetic Resonance Imaging: Principles and Applications*, (Williams and Wilkins, Baltimore 1986). Contemplated MRI techniques include, but are not limited to, nuclear magnetic resonance (NMR) and electronic spin resonance (ESR). The preferred imaging modality is NMR.

Figure 1:
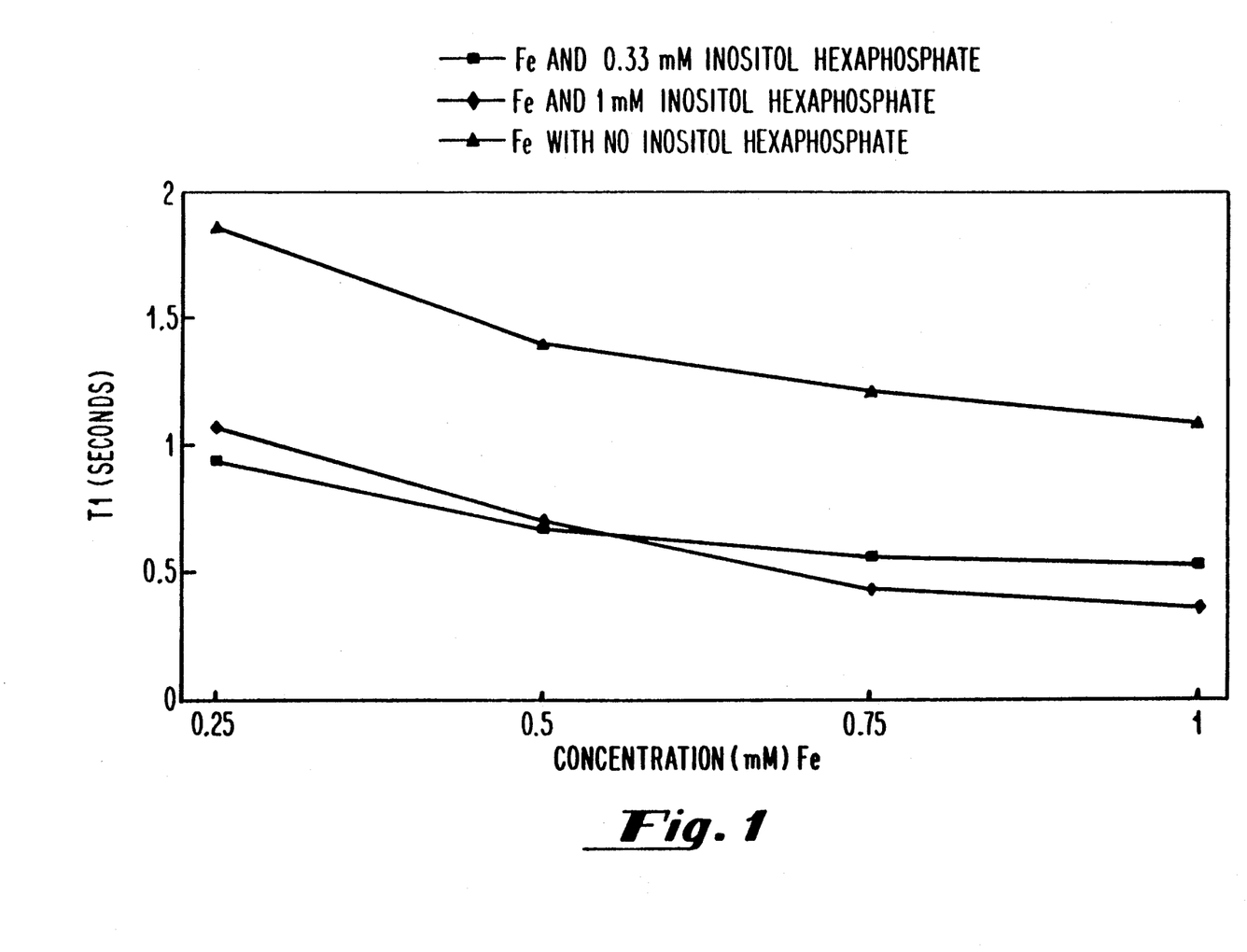
FIG. 1. The T1 values for solutions of ferric citrate in combination with a concentration of 0.33 or 1.0 millimolar inositol hexaphosphate, and the T1 values for solutions of ferric citrate without inositol hexaphosphate, are shown. In each solution, 2 weight % cellulose was present, as well as 0.25 weight % xanthum gum. As the figure reveals, there is an approximately three-fold effect on the T1 relaxation times caused by the ferric iron and inositol hexaphosphate combination, as compared to ferric iron without the inositol hexaphosphate.
Figure 6A:
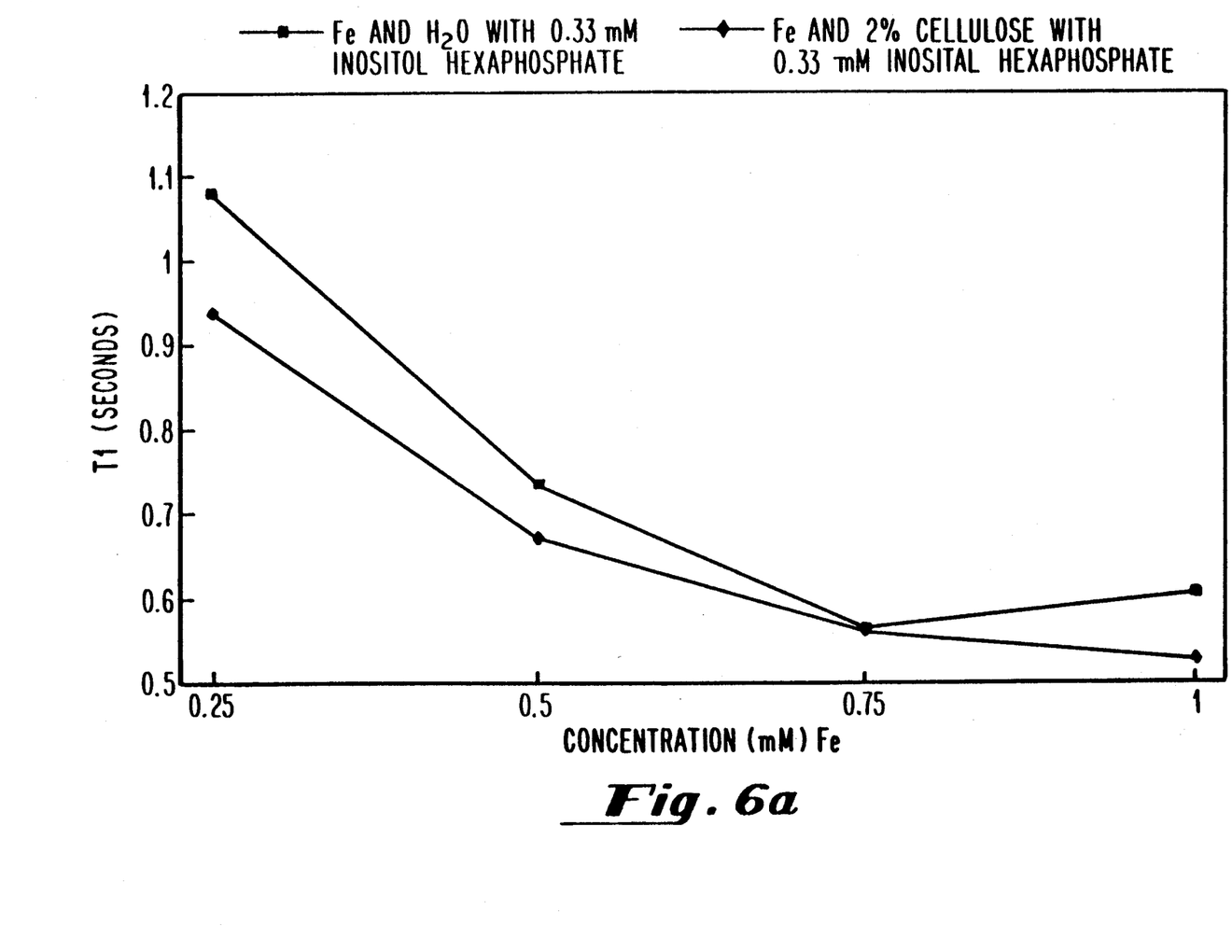
FIGS. 6a and 6b. The effect on T1 of ferric iron with inositol hexaphosphate, and ferric iron with inositol hexaphosphate and 2 weight % of cellulose (FIG. 6a), and the effect on T2 of ferric iron with 2 weight % of cellulose and 0.25 weight % xanthan gum, and ferric iron with inositol hexaphosphate and 2 weight % cellulose and a 0.25 weight % xanthan gum (FIG. 6b) is shown. The addition of 2 weight % cellulose to a solution of ferric iron and inositol hexaphosphate causes a slight increase in T1 relaxivity. The presence of cellulose has an even greater effect on T2 relaxivity.
Figure 6B:
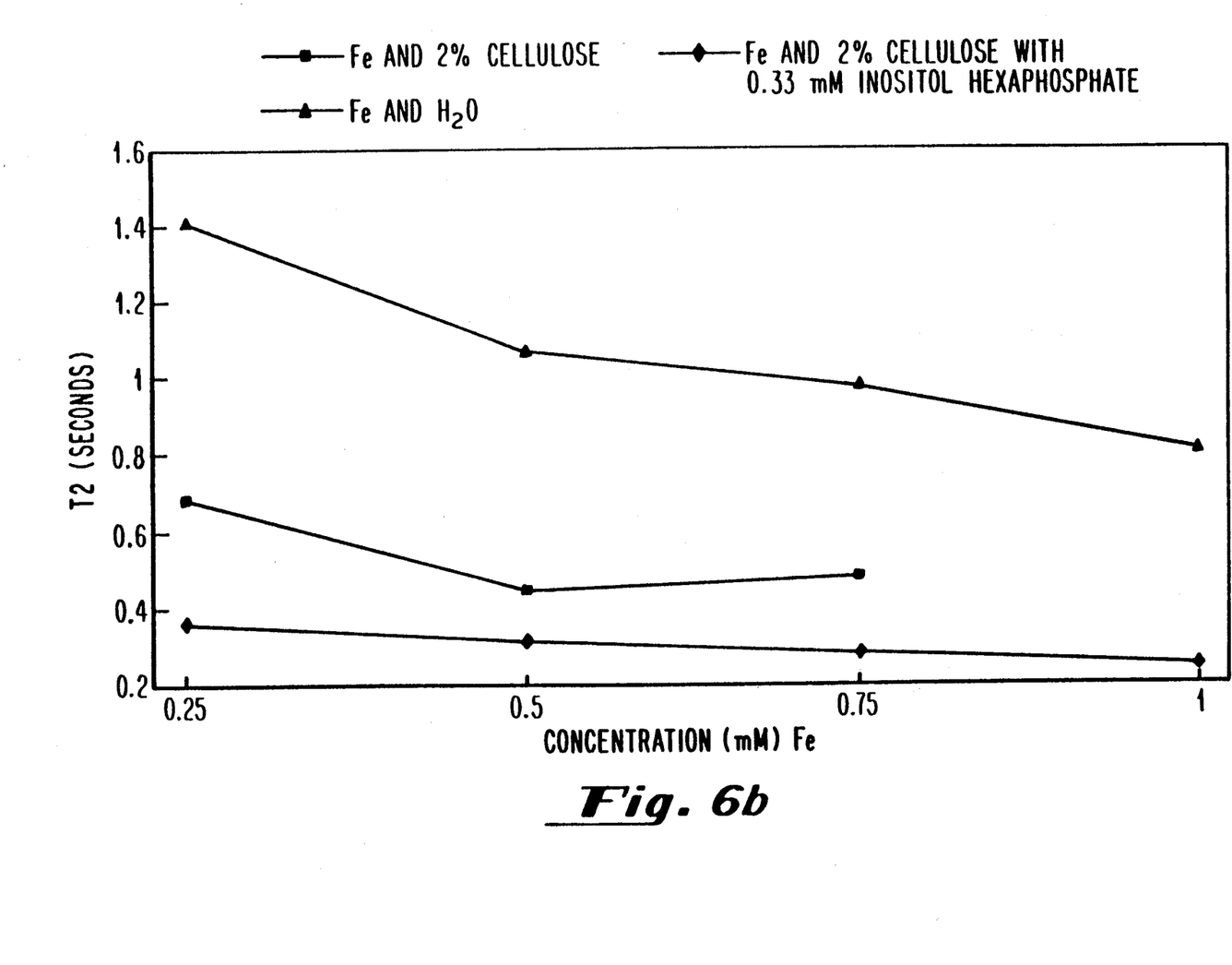

Phosphorylated compounds utilized in the gastrointenstinal imaging methods of the present invention have been found to enhance the relaxivity of the paramagnetic ions with which they are combined. In the case of the combination of the phosphorylated alicyclic compound inositol hexaphosphate with the paramagnetic agent ferric iron, for example, relaxivity in the gastrointestinal region was found to increase by a factor of almost three-fold in comparison with the use of ferric iron alone (FIG. 1). As shown in FIG. 6, the T2 relaxation effects may be further enhanced by using a combination of inositol hexaphosphate and cellulose with the paramagnetic ion ferric iron. The combination of phosphorylated compound and paramagnetic ion of the present invention may act to both increase signal intensity on T1 weighted gastrointestinal images and decreases signal intensity on T2 weighted gastrointestinal images, providing both positive and negative contrast, an ideal characteristic for a gastrointestinal contrast agent.

The greatly enhanced relaxivity resulting from, for example, the combination of ferric iron with inositol hexaphosphate in gastrointestinal imaging, has never been reported and is indeed unexpected. Generally, when a paramagnetic ion is bound by a complexation agent (a ligand), there is a reduction in relaxivity caused by shielding of the paramagnetic centers from water. An example is gadolinium-DTPA wherein the complex has about one-half the relaxivity of free gadolinium ion. It is unexpected that a phosphorylated compound, such as, for example, inositol hexaphosphate, might improve the relaxivity of, for example, iron or manganese so dramatically.

Figure 2:
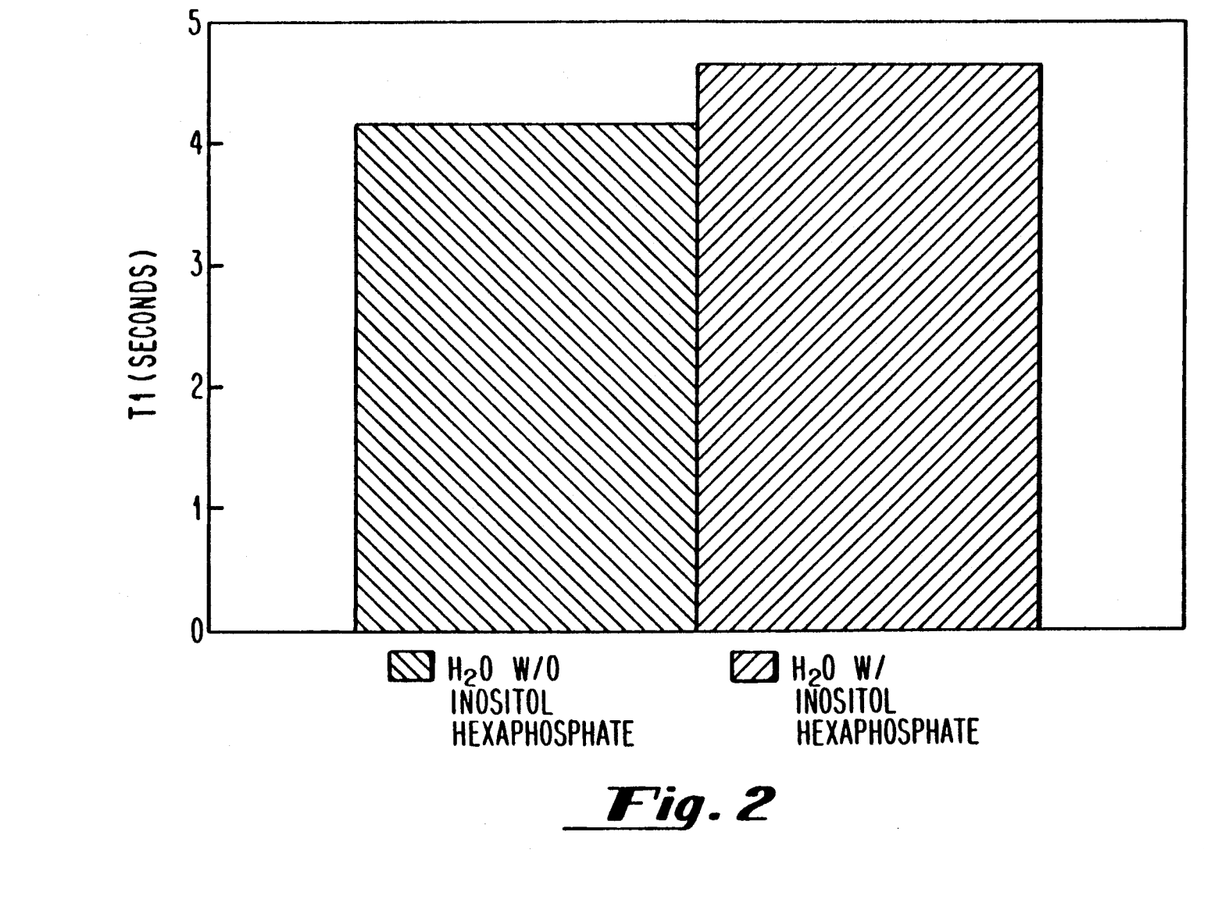
FIG. 2. The T1 relaxation time of water alone, and water with 0.33 millimolar inositol hexaphosphate are shown. The addition of inositol hexaphosphate to the water has no appreciable effect on T1 relaxivity, at most causing a mild prolongation of T1, but showing no improvement in T1 relaxivity.
Figure 3A:
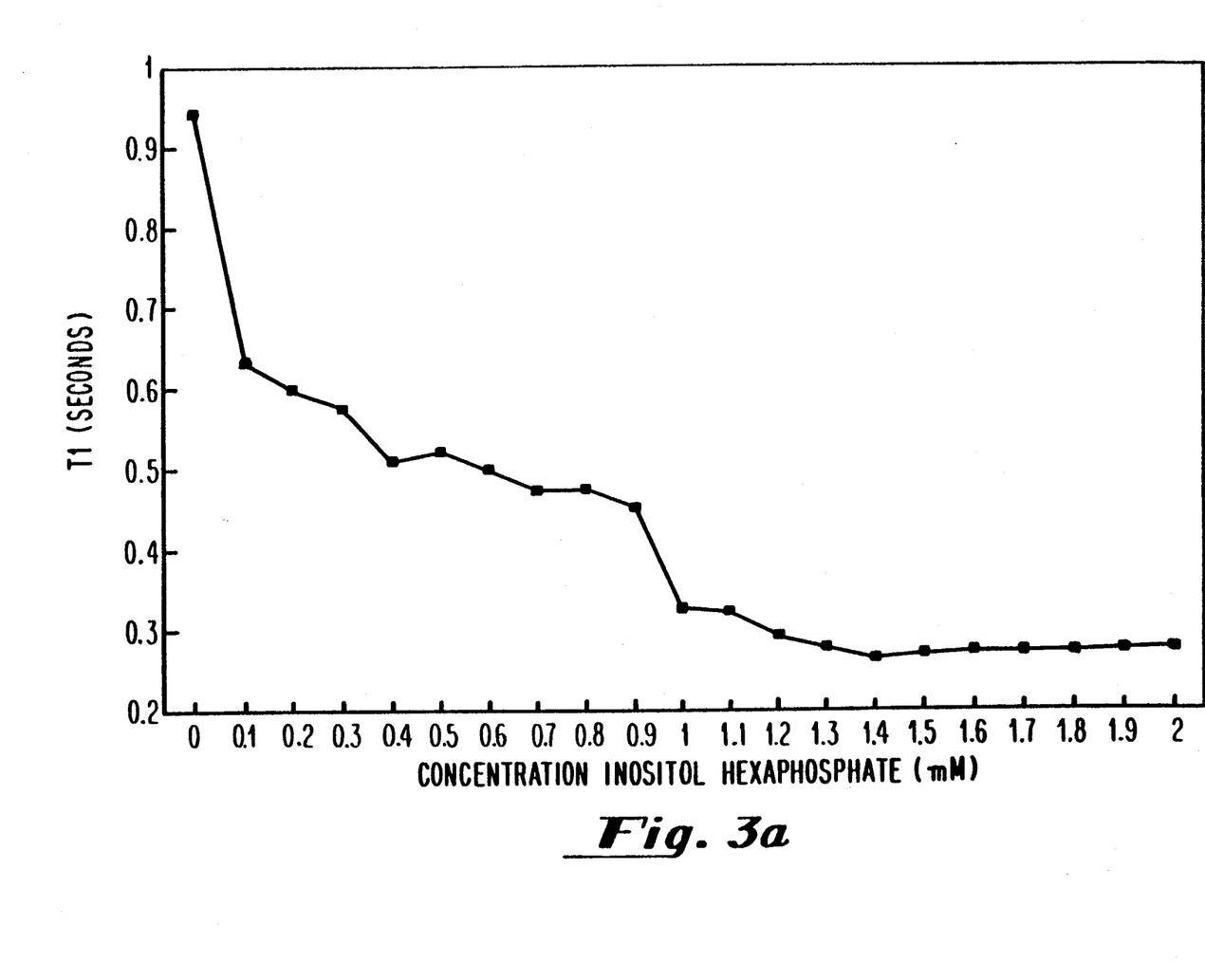
FIGS. 3a and 3b. The T1 (FIG. 3a) and T2 (FIG. 3b) relaxation times of 1.0 millimolar concentration of ferric iron in combination with inositol hexaphosphate concentrations varying between 0.1 and 2.0 millimolar are shown. The optimum ratio of ferric iron to inositol hexaphosphate appears to be about 1 to 1 for maximizing relaxivity.
Figure 3B:
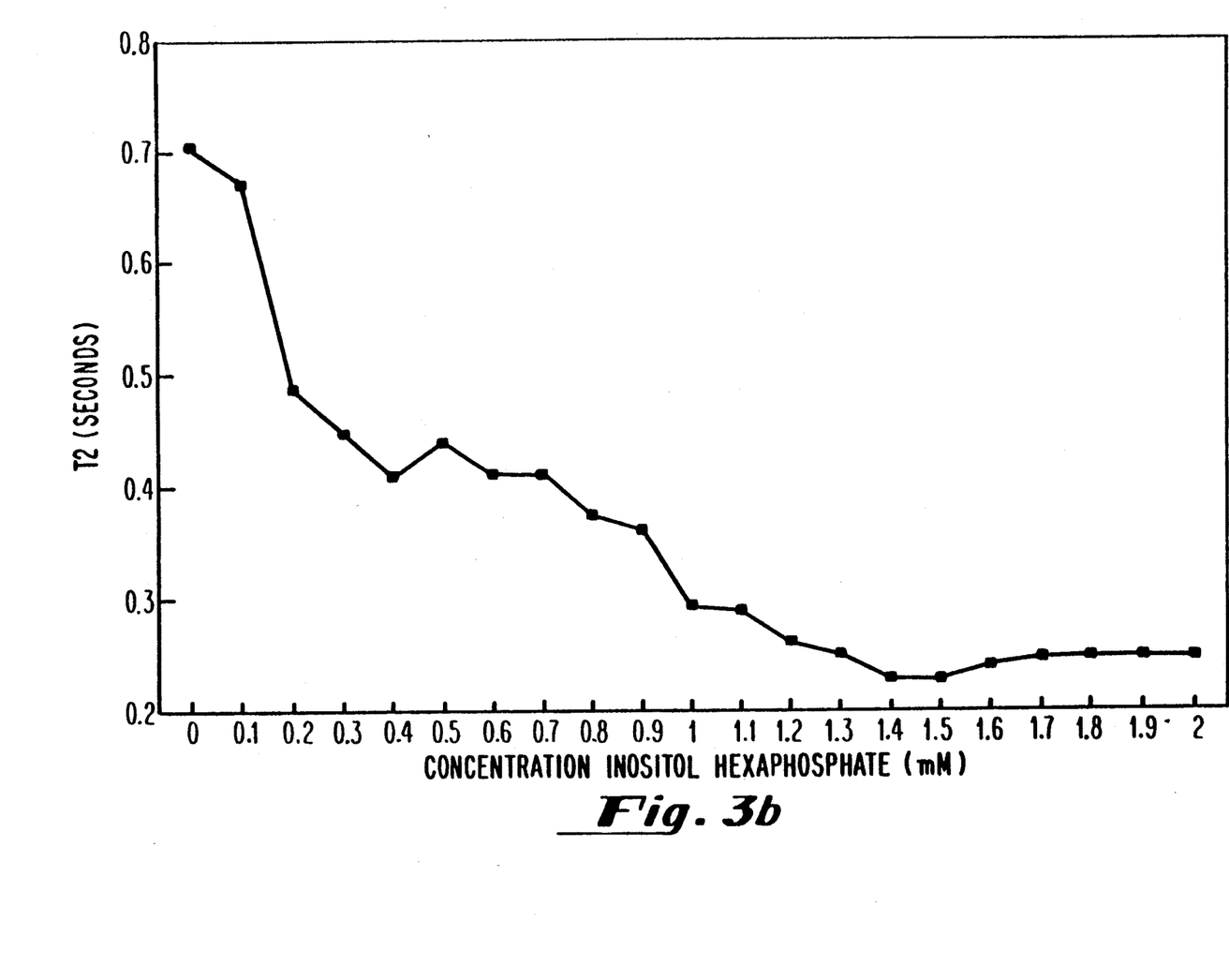
Figure 4A:
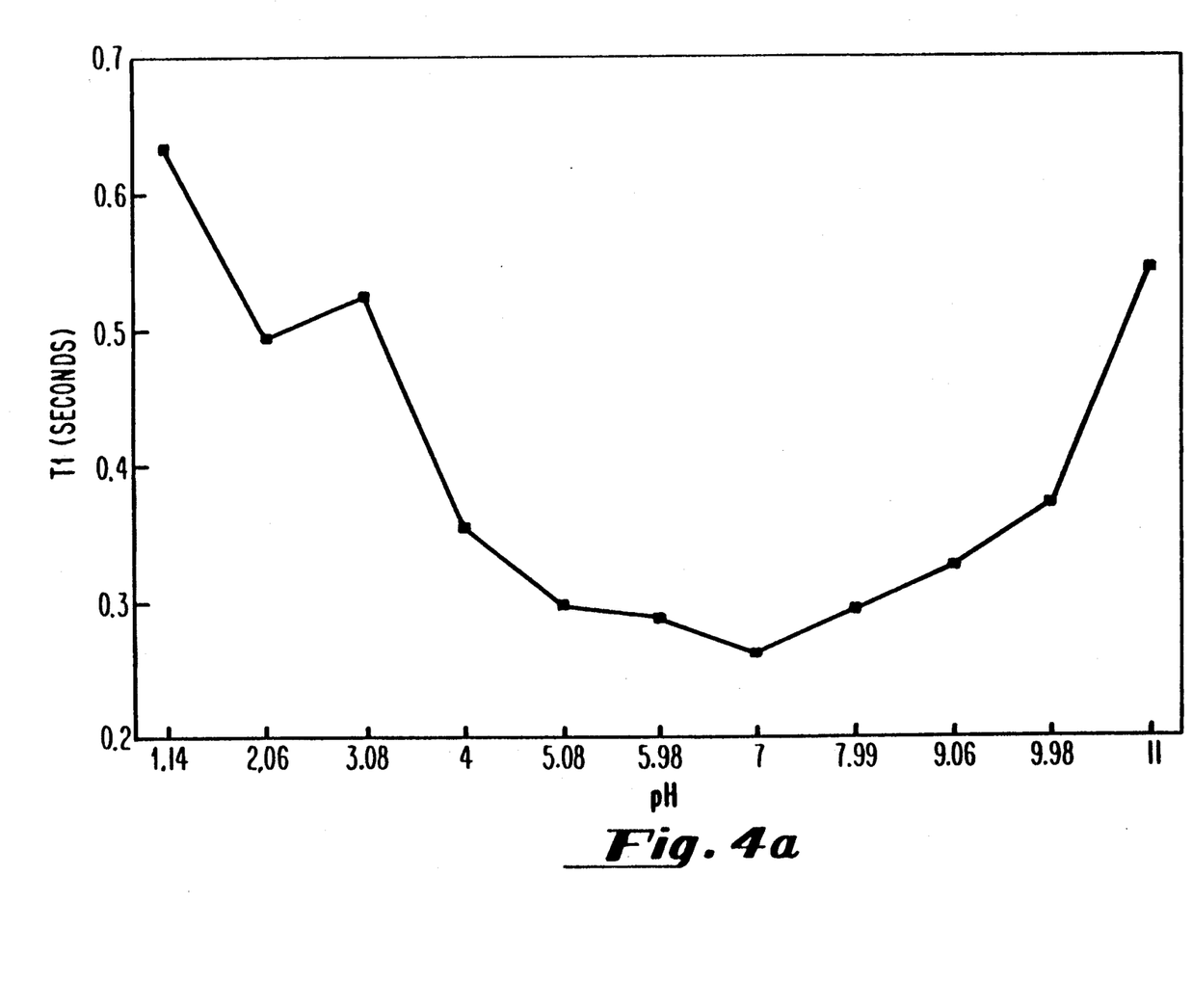
FIGS. 4a and 4b. The T1 (FIG. 4a) and T2 (FIG. 4b) relaxation times of 1 millimolar solutions of ferric iron with 1 millimolar inositol hexaphosphate at varying pHs are shown. The T1 and T2 relaxation times are appreciably shorter between pH 4 and pH 10, which reflects a stronger interaction with inositol hexaphosphate with ferric iron over this range of pH values.
Figure 4B:
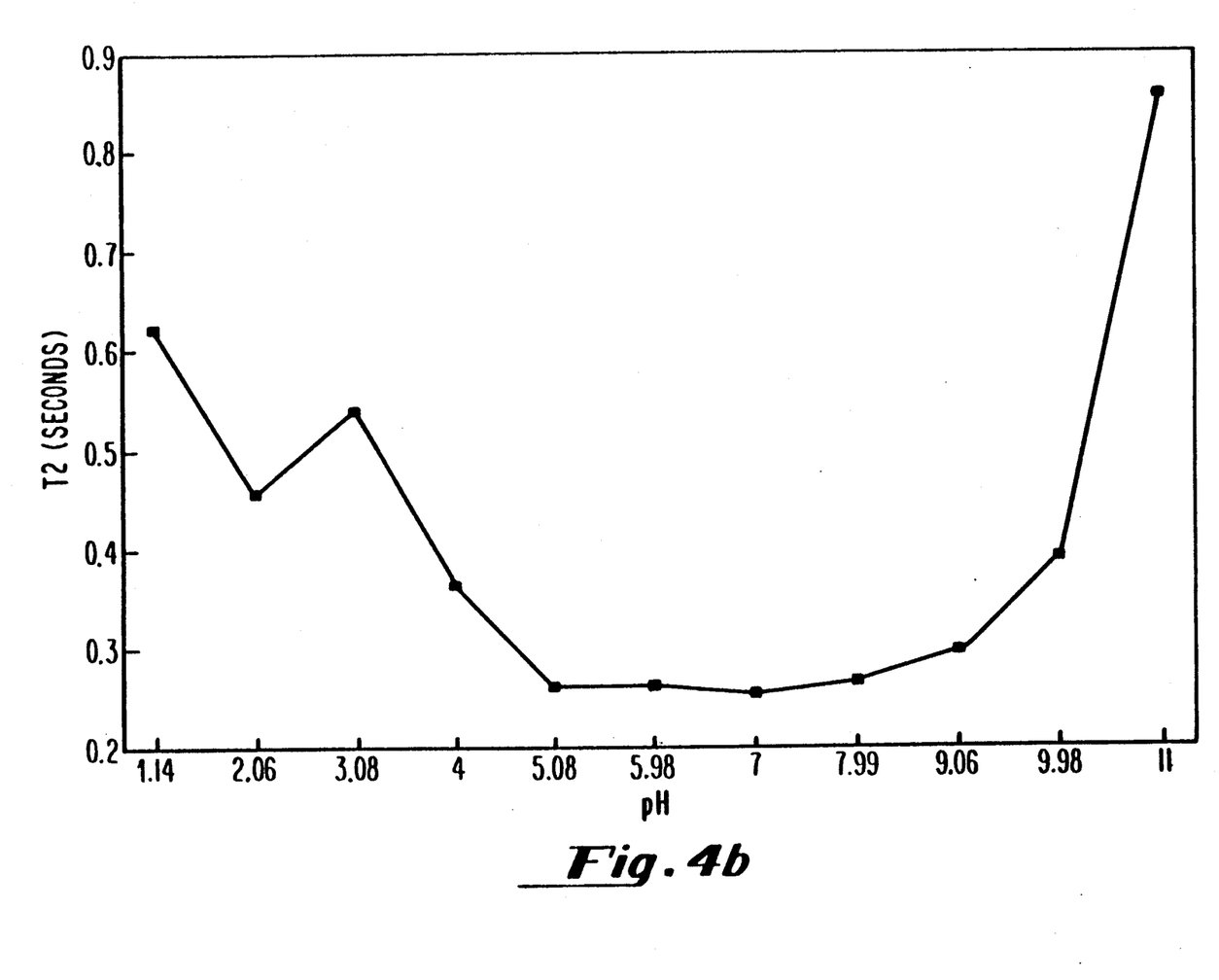
Figure 5:
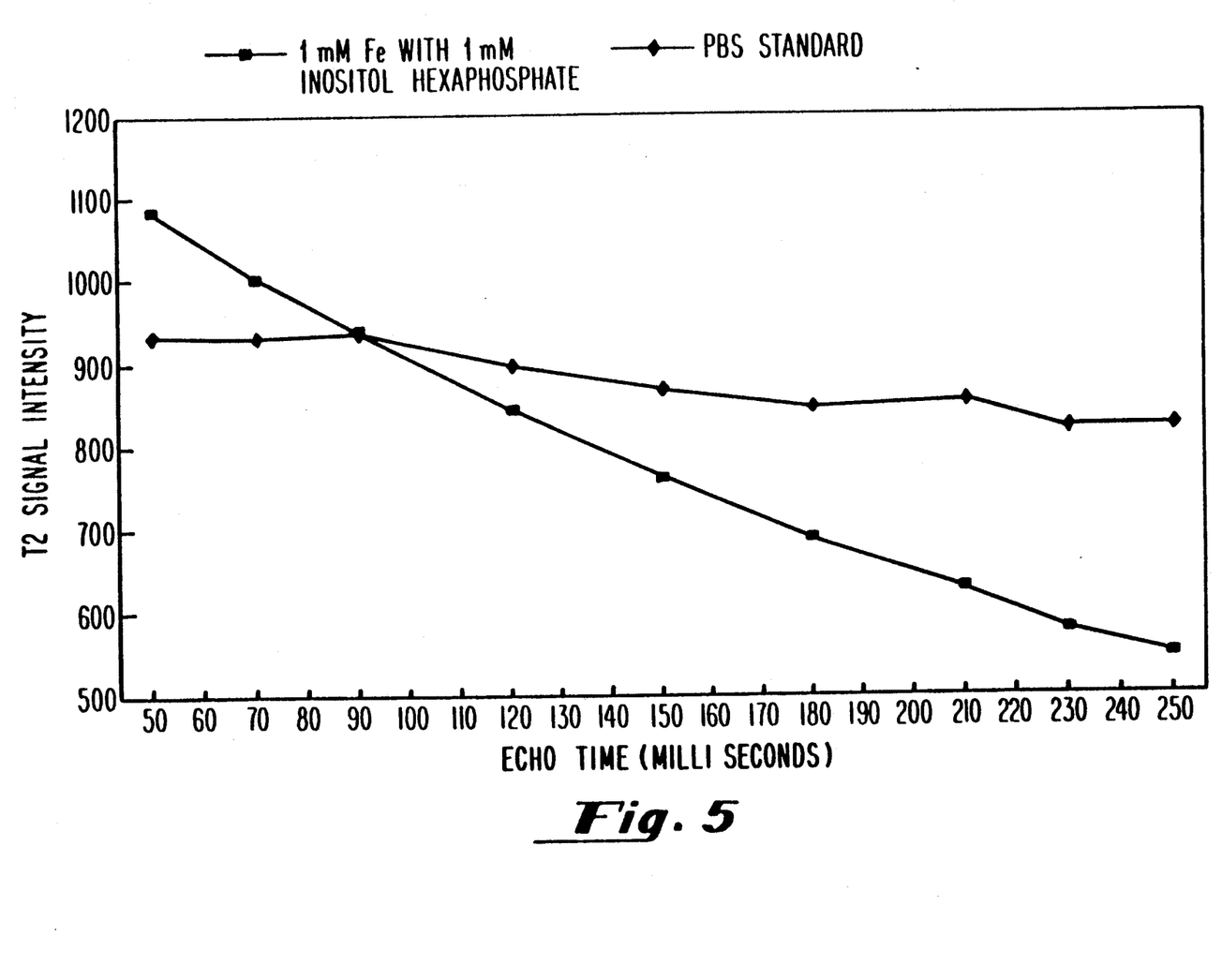
FIG. 5. The T2 signal intensity on magnetic resonance images is shown for phosphate buffered saline (PBS) and a solution of 1 millimolar ferric iron with 1 millimolar inositol hexaphosphate at a constant TR and at echo times varying from 50 to 250 milliseconds. As shown in this figure, the signal intensity of the ferric iron/inositol hexaphosphate contrast agent falls much more rapidly than saline. On a T2 weighted image of the gastrointestinal tract containing concentrations of ferric iron/inositol hexaphosphates greater than 1 millimolar (not shown), there was an appreciable decrease in signal intensity of the fluid in the bowel.
Figure 7:
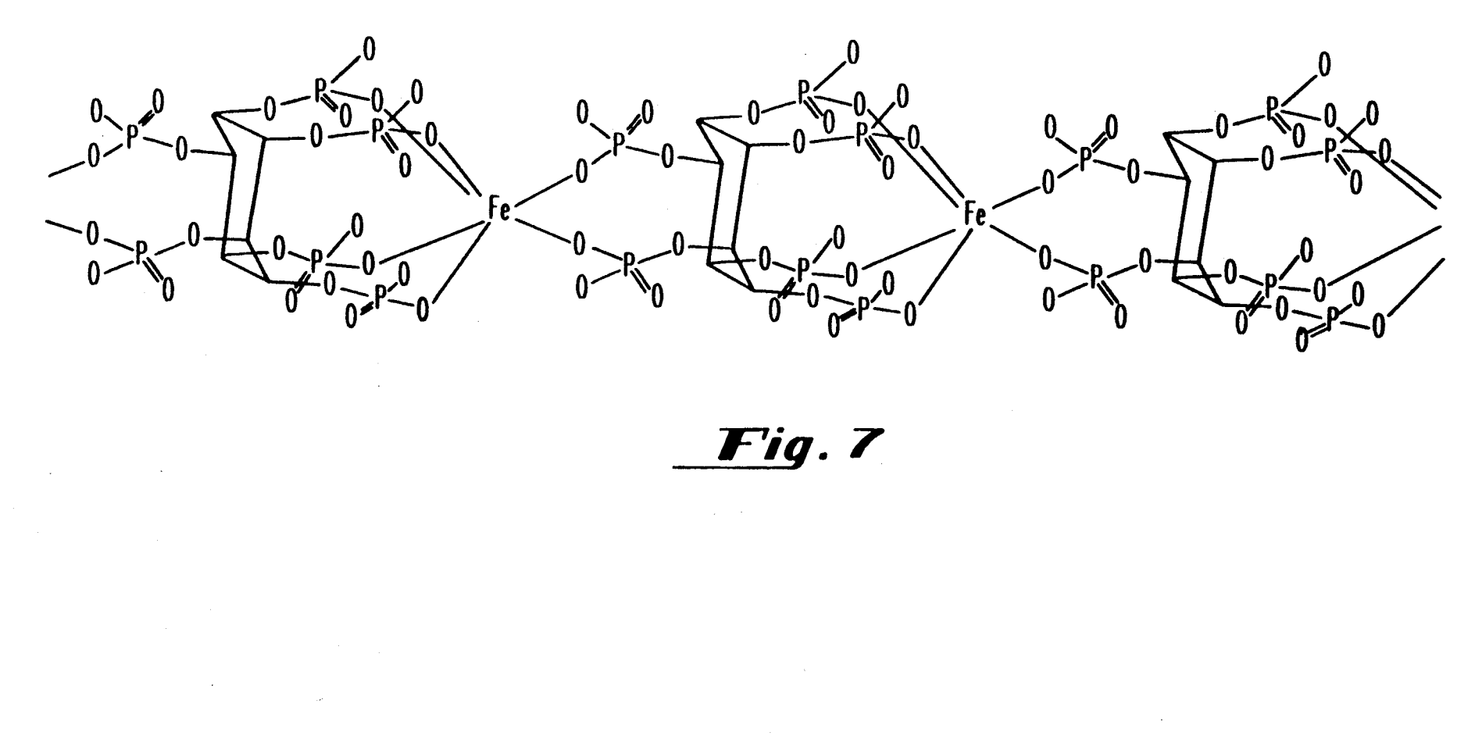
FIG. 7. The stacking phenomenon that is believed to occur where an inositol hexaphosphate is combined with a paramagnetic ion is shown. In accordance with this theory, the inositol hexaphosphate is believed to bind to a paramagnetic ion, which in turn binds to another polyphosphorylated compound, which in turn may bind to another paramagnetic ion, which in turn may bind to another phosphorylated compound, and so on, forming a copolymer of varying length of the phosphorylated compound and the paramagnetic ion. The stacking of three inositol hexaphosphate compounds with the paramagnetic ion iron is shown for illustration purposes.

Although not intending to be bound by any theory or mechanism of operation, it is believed that the phosphorylated compounds employed in the gastrointestinal imaging methods of the invention may act to improve the relaxivity of the paramagnetic ions by slowing the correlation time of the iron, that is, by slowing down the rate at which the iron is tumbling in solution, rather than by some cross relaxation mechanism. As shown in FIG. 2, inositol hexaphosphate appears to have little, if any, significant effect on the relaxation rate of water. If cross-relaxation were the dominant mechanism responsible for the increase in relaxivity with the iron plus inositol hexaphosphate contrast medium, then the inositol hexaphosphate alone should have some measure of relaxation effect on water. Moreover, when the inositol hexaphosphate is added to the solution of ferric iron as shown in FIG. 1, there is a dose related effect on relaxivity. This change in relaxivity may reflect the inositol hexaphosphate binding the iron and slowing the tumbling rates, resulting in a more favorable correlation time of the iron such that the relaxivity of the iron is enhanced. Further to this theory, it is believed that when the paramagnetic ions are added to the polyphosphorylated aliphatic and alicyclic compounds, a stacking phenomenon tends to occur wherein a polyphosphorylated compound binds to a paramagnetic ion, which in turn binds to another polyphosphorylated compound, which in turn binds to another paramagnetic ion, which in turn binds to another phosphorylated compound, and so on, forming in essence a "copolymer" of the phosphorylated compound "monomer" and the paramagnetic ion "monomer". This stacking phenomenon ("copolymer" formation) is schematically illustrated in FIG. 7. It is believed that the stacking phenomenon may, at least in part, account for highly diagnostically effective properties of the preferred compounds of the present invention, providing slower tumbling rates, more favorable correlation times and enhanced relaxivity.

Another advantage of the present invention is that a smaller amount of the paramagnetic ion is absorbed in the gastrointestinal tract when the phosphorylated compounds are employed in combination therewith. For example, the absorption of ferric iron in the gastrointestinal tract was found to decrease by over 80% when employed in combination with inositol hexaphosphate. One benefit to patients utilizing the present invention is that a lower dose of contrast agent is needed to produce clinically useful contrast enhancement of the gastrointestinal tract. It is possible to achieve the same pattern of enhancement in the gastrointestinal region using paramagnetic agent without a phosphorylated compound, but an approximately three-fold higher concentration of paramagnetic ion may have to be utilized, and such a high amount of paramagnetic ion may prove toxic. Moreover, where only a paramagnetic agent is used, absorption of the paramagnetic ion may be a problem, not only in causing toxicity, but may also result in diminished contrast in the distal portion of the gastrointestinal tract The present invention is further described in the following Examples. These Examples are not to be construed as limiting the scope of the appended claims.

EXAMPLES

Example 1

A contrast medium was formulated by preparing a 900 cc aqueous solution containing 120 mg of ferric ammonium citrate with 720 mg of inositol hexaphosphate (1 to 1 molar ratio of ferric iron to inositol hexaphosphate), and was orally ingested by a human test volunteer. T1 and T2 weighted spin echo images of the abdomen were obtained using magnetic resonance imaging. High signal intensity was observed on both the T1 and T2 weighted images.

Example 2

A contrast medium was formulated by preparing a 900 cc aqueous solution containing 200 mg of ferric ammonium citrate with 1200 mg of inositol hexaphosphate (1 to 1 molar ratio of ferric iron to inositol hexaphosphate), and was orally ingested by a human test volunteer. Images were taken of the gastrointestinal region of the volunteer using magnetic resonance imaging, both pre and post ingestion. The images revealed greatly enhanced contrast of the gastrointestinal region post ingestion, particularly in the stomach and small intestine (including the duodenum) areas, with high signal intensity on the T1 weighted images (high positive contrast) and somewhat low signal intensity (slight negative contrast) on the T2 weighted images in the gastrointestinal lumen being observed.

Example 3

The procedures of Example 2 were substantially repeated, except that in addition to the ferric ammonium citrate and inositol hexaphosphate, 9 g of phosphorylated cellulose (1% by weight) was added to the solution. The results, following imaging, were substantially similar to Example 1, except that even lower signal intensity (higher negative contrast) on the T2 weighted images was observed.

Example 4

A contrast medium was formulated by preparing a 1 liter aqueous solution containing 5.6 mg of manganese (II) chloride (approximately 0.1 mM manganese) and 0.3 mM inositol hexaphosphate (an approximate 1 to 3 molar ratio of manganese to inositol hexaphosphate), and was orally ingested by a human test volunteer. Images were taken of the gastrointestinal region of the volunteer using magnetic resonance imaging. The resultant images showed slight high signal intensity on the T1 weighted images, but no appreciable contrast on the T2 weighted images.

Example 5

Three separate contrast media were formulated by preparing aqueous solutions containing, respectively, 20, 30 and 40 mg of manganese (II) per liter, each containing a three-fold excess of inositol hexaphosphate in an iso-osmotic solution. The osmolality of the solution was adjusted to about 300 mosm using sorbitol and polyethylene glycol. In addition, approximately 2 grams of vitamin C per liter was added to each solution to minimize oxidation of the Mn (II) to the less favorable relaxation state of Mn (III). Xanthan gum (0.25 weight %) was also added. Each solution was then ingested by a different human test volunteer, and images were taken of the gastrointestinal region using magnetic resonance imaging. In each case, the solution showed high signal intensity on the T1 weighted images of the bowel with the region of enhancement extending from the stomach into the distal small bowel. On the T2 weighted images, the preparations with 30 and 40 mg of manganese per liter showed low signal intensity on the T2 weighted images which was more pronounced for the concentration of 40 mg per liter of manganese. Even at a concentration of 40 mg manganese per liter, however, the distal portion of the small bowel still appeared bright on the T2 weighted images.

Example 6

Three separate contrast media were formulated by preparing aqueous solutions in three separate bottles of 300 cc each. Bottle #1 contained 60 mg of manganese (II) and 60 mg of iron (II) per liter, and a three-fold excess inositol hexaphosphate in an iso-osmotic solution. Bottle #2 contained 50 mg of manganese (II) and 50 mg of iron (II) per liter, and a three-fold excess inositol hexaphosphate in an iso-osmotic solution. Bottle #3 contained 40 mg of manganese (II) and 40 mg of iron (II) per liter, and a three-fold excess inositol hexaphosphate in an iso-osmotic solution. The contents of each of the three bottles were then ingested over a short period of time by a human test volunteer, in the order of bottle #1 first, then bottle #2, and finally bottle #3, and images were taken of the gastrointestinal region using magnetic resonance imaging. Enhancement was found to be much more uniform with positive contrast on T1 and negative contrast on T2 weighted images. Enhancement in the colon area, however, was less than desired.

Example 7

Three separate contrast media were formulated by preparing aqueous solutions in three separate bottles of 300 cc each. Bottle #1 contained 75 mg of manganese (II), 75 mg of iron (II) per liter, a three-fold excess inositol hexaphosphate, 2 g vitamin C, 0.75 weight % algin, and 0.25 weight % xanthan gum. Bottle #2 contained 60 mg of manganese (II), 60 mg of iron (II) per liter, a three-fold excess inositol hexaphosphate, 2 g vitamin C, 0.5 weight % algin, and 0.25 weight % xanthan gum. Bottle #3 contained 50 mg of manganese (II), 50 mg of iron (II) per liter, a three-fold excess inositol hexaphosphate, 2 g vitamin C, 0.3 weight % algin, and 0.25 weight % xanthan gum. Osmolality of each solution was adjusted to about 300 mosm using 1% sorbitol and 2% polyethylene glycol in each bottle. The contents of each of the three bottles were then ingested over a short period of time by a human test volunteer, in the order of bottle #1 first, then bottle #2, and finally bottle #3, and images were taken of the gastrointestinal region using magnetic resonance imaging. Enhancement was found to be even much more uniform than in Example 6, with positive contrast on T1 and negative contrast on T2 weighted images. Enhancement was visualized throughout the entire gastrointestinal tract.

Various modifications of the invention in addition to those shown and described herein will be apparent to those skilled in the art from the foregoing description. Such modifications are also intended to fall within the scope of the appended claims.

What is claimed is:

1. A method of providing an image of the gastrointestinal region of a patient comprising
   (a) administering to the patient a diagnostically effective amount of a contrast medium comprising (i) a polyphosphorylated acyclic compound comprising at least five uninterrupted carbon atoms, wherein said carbon atoms collectively contain at least two phosphate substituents, and (ii) a paramagnetic ion, and
   (b) scanning the patient using magnetic resonance imaging to obtain visible images of that region.

2. A method according to claim 1 wherein said polyphosphorylated acyclic compound is polyphosphorylated polyvinyl alcohol.

3. A method according to claim 1 wherein said polyphosphorylated acyclic compound is selected from the group consisting of polyphosphorylated polyvinyl alcohol, polyphosphorylated polyacrylic acid, polyphosphorylated polymethacrylic acid, and polyphosphorylated copolymers of acrylic acid and methacrylic acid.

4. A method according to claim 1 wherein said paramagnetic ion is selected from the group consisting of transition, lanthanide and actinide elements.

5. A method according to claim 4 wherein said paramagnetic ion is selected from the group consisting of Gd(III), Mn(II), Cu(II), Cr(III), Fe(II), Fe(III), Co(II), Er(II), Ni(II), Eu(III), Yb(III), and Dy(III).

6. A method according to claim 5 wherein said paramagnetic ion is selected from the group consisting of Fe(III) and Mn(II).

7. A method for diagnosing the presence of diseased tissue in the gastrointestinal region of a patient comprising
   (a) administering to the patient a diagnostically effective amount of a contrast medium comprising (i) a polyphosphorylated acyclic compound comprising at least five uninterrupted carbon atoms, wherein said carbon atoms collectively contain at least two phosphate substituents, and (ii) a paramagnetic ion, and
   (b) scanning the patient using magnetic resonance imaging to obtain visible images of any diseased tissue in the patient.

8. A method according to claim 7 wherein said polyphosphorylated acyclic compound is polyphosphorylated polyvinyl alcohol.

9. A method according to claim 7 wherein said polyphosphorylated acyclic compound is selected from the group consisting of polyphosphorylated polyvinyl alcohol, polyphosphorylated polyacrylic acid, polyphosphorylated polymethacrylic acid, and polyphosphorylated copolymers of acrylic and methacrylic acid.

10. A method according to claim 7 wherein said paramagnetic ion is selected from the group consisting of transition, lanthanide and actinide elements.

11. A method according to claim 10 wherein said paramagnetic ion is selected from the group consisting of Gd(III), Mn(II), Cu(II), Cr(III), Fe(II), Fe(III), Co(II), Er(II), Ni(II), Eu(III), Yb(III), and Dy(III).

12. A method according to claim 11 wherein said paramagnetic ion is selected from the group consisting of Fe(III) and Mn(II).

* * * * *